United States Patent
Hutchinson

(10) Patent No.: US 10,779,771 B2
(45) Date of Patent: Sep. 22, 2020

(54) SIGNAL PROCESSING METHOD AND APPARATUS

(71) Applicant: OXEHEALTH LIMITED, Oxford, Oxfordshire (GB)

(72) Inventor: Nicholas Dunkley Hutchinson, Oxford (GB)

(73) Assignee: OXEHEALTH LIMITED, London (GB)

( * ) Notice: Subject to any disclaimer, the term of this patent is extended or adjusted under 35 U.S.C. 154(b) by 82 days.

(21) Appl. No.: 16/071,542

(22) PCT Filed: Jan. 19, 2017

(86) PCT No.: PCT/GB2017/050126
§ 371 (c)(1),
(2) Date: Jul. 20, 2018

(87) PCT Pub. No.: WO2017/125742
PCT Pub. Date: Jul. 27, 2017

(65) Prior Publication Data
US 2019/0029600 A1    Jan. 31, 2019

(30) Foreign Application Priority Data
Jan. 22, 2016   (GB) .................................. 1601217.1

(51) Int. Cl.
*A61B 5/00*     (2006.01)
*A61B 5/024*    (2006.01)
(Continued)

(52) U.S. Cl.
CPC ........ *A61B 5/7225* (2013.01); *A61B 5/02416* (2013.01); *A61B 5/08* (2013.01);
(Continued)

(58) Field of Classification Search
CPC ..... A61B 5/7225; A61B 5/02416; A61B 5/08; A61B 5/1128; A61B 5/7239; G06T 7/20
(Continued)

(56) References Cited

U.S. PATENT DOCUMENTS 8,855,384 B2   10/2014   Kyal et al.
8,965,090 B1    2/2015   Khachaturian et al.
(Continued)

FOREIGN PATENT DOCUMENTS

EP    0615245 A2    9/1994
EP    0919184 A1    6/1999
(Continued)

OTHER PUBLICATIONS

Kumar-DistancePPG: Robust non-contact vital signs monitoring using a camera, Optical Society of America (2015).
(Continued)

*Primary Examiner* — Tan V Mai
(74) *Attorney, Agent, or Firm* — Harness, Dickey & Pierce, P.L.C.

(57) ABSTRACT

A method and apparatus which combines multiple simultaneous signals thought to contain a common periodic component by performing principal component analysis on each of the multiple signals, finding the weight of the first principal component, and then adding the multiple signals together in a weighted sum according to the weight of the first principal component. The method and apparatus further includes a way of combining signals from successive overlapping time windows in real time by differentiating the signal and forming as each output signal sample the value of the preceding signal sample summed with the differential of the signal, weighted by weights based on the amplitude of the differential signal at that time point.

17 Claims, 7 Drawing Sheets

(51) Int. Cl.
*A61B 5/11* (2006.01)
*A61B 5/08* (2006.01)
*G06T 7/20* (2017.01)
*A61B 5/113* (2006.01)

(52) U.S. Cl.
CPC .......... *A61B 5/1128* (2013.01); *A61B 5/7239* (2013.01); *G06T 7/20* (2013.01); *A61B 5/024* (2013.01); *A61B 5/0816* (2013.01); *A61B 5/1135* (2013.01); *G06T 2207/10016* (2013.01)

(58) Field of Classification Search
USPC ........................................................ 708/300
See application file for complete search history.

(56) References Cited

U.S. PATENT DOCUMENTS

| | | | |
|---|---|---|---|
| 9,036,877 | B2 | 5/2015 | Kyal et al. |
| 10,034,979 | B2 | 7/2018 | Bechtel et al. |
| 10,292,662 | B2 | 5/2019 | Kirenko |
| 2002/0106709 | A1 | 8/2002 | Potts et al. |
| 2002/0180870 | A1 | 12/2002 | Chen |
| 2003/0138149 | A1 | 7/2003 | Iizuka et al. |
| 2003/0228032 | A1 | 12/2003 | Rui et al. |
| 2005/0197590 | A1* | 9/2005 | Osorio ................... A61B 5/048 600/544 |
| 2006/0058618 | A1 | 3/2006 | Nishiura |
| 2007/0156060 | A1 | 7/2007 | Cervantes |
| 2007/0195931 | A1 | 8/2007 | Ohishi |
| 2008/0292151 | A1 | 11/2008 | Kurtz et al. |
| 2009/0216499 | A1 | 8/2009 | Tobola et al. |
| 2010/0049064 | A1 | 2/2010 | Bodmer et al. |
| 2010/0074475 | A1 | 3/2010 | Chouno |
| 2010/0298656 | A1 | 11/2010 | McCombie et al. |
| 2011/0046498 | A1 | 2/2011 | Klap et al. |
| 2011/0150274 | A1 | 6/2011 | Patwardhan et al. |
| 2011/0251493 | A1 | 10/2011 | Poh et al. |
| 2011/0311143 | A1 | 12/2011 | Cennini et al. |
| 2012/0141000 | A1 | 6/2012 | Jeanne et al. |
| 2012/0213405 | A1 | 8/2012 | Sasaki |
| 2012/0242819 | A1 | 9/2012 | Schamp |
| 2013/0138009 | A1 | 5/2013 | Nierenberg et al. |
| 2013/0324875 | A1 | 12/2013 | Mestha et al. |
| 2014/0003690 | A1 | 1/2014 | Razeto et al. |
| 2014/0023235 | A1 | 1/2014 | Cennini et al. |
| 2014/0037163 | A1 | 2/2014 | Kirenko et al. |
| 2014/0037166 | A1 | 2/2014 | De Haan et al. |
| 2014/0236036 | A1 | 8/2014 | de Haan et al. |
| 2014/0276099 | A1 | 9/2014 | Kirenko et al. |
| 2014/0276104 | A1 | 9/2014 | Tao et al. |
| 2014/0334697 | A1 | 11/2014 | Kersten et al. |
| 2014/0371599 | A1 | 12/2014 | Wu et al. |
| 2014/0371635 | A1 | 12/2014 | Shinar et al. |
| 2014/0378842 | A1 | 12/2014 | Xu et al. |
| 2015/0005646 | A1 | 1/2015 | Balakrishnan et al. |
| 2015/0063708 | A1 | 3/2015 | Sripadarao et al. |
| 2015/0148687 | A1 | 5/2015 | Kitajima et al. |
| 2015/0208987 | A1 | 7/2015 | Shan et al. |
| 2015/0221069 | A1 | 8/2015 | Shaburova et al. |
| 2015/0250391 | A1 | 9/2015 | Kyal et al. |
| 2015/0363361 | A1 | 12/2015 | Kniazev |
| 2016/0106340 | A1 | 4/2016 | Mestha et al. |
| 2016/0125260 | A1 | 5/2016 | Huang et al. |
| 2016/0132732 | A1 | 5/2016 | Gunther et al. |
| 2016/0220128 | A1 | 8/2016 | Den Brinker et al. |
| 2016/0253820 | A1 | 9/2016 | Jeanne et al. |
| 2016/0310067 | A1 | 10/2016 | Heinrich et al. |
| 2017/0007185 | A1 | 1/2017 | Lin et al. |
| 2017/0042432 | A1 | 2/2017 | Adib et al. |
| 2017/0224256 | A1 | 8/2017 | Kirenko |
| 2017/0238805 | A1 | 8/2017 | Addison et al. |
| 2017/0238842 | A1 | 8/2017 | Jacquel et al. |
| 2018/0085010 | A1 | 3/2018 | Jones et al. |
| 2018/0279885 | A1 | 10/2018 | Bulut |
| 2019/0000391 | A1 | 1/2019 | De Haan et al. |
| 2019/0267040 | A1 | 8/2019 | Ikeda et al. |

FOREIGN PATENT DOCUMENTS

| | | | |
|---|---|---|---|
| EP | 1571594 | A2 | 9/2005 |
| EP | 2767233 | A1 | 8/2014 |
| EP | 2976998 | A1 | 1/2016 |
| EP | 2988274 | A2 | 2/2016 |
| EP | 3073905 | A1 | 10/2016 |
| EP | 3207862 | A1 | 8/2017 |
| JP | 2011130996 | A | 7/2011 |
| WO | WO-2010/100593 | A1 | 9/2010 |
| WO | WO-2010/115939 | A2 | 10/2010 |
| WO | WO-2011021128 | A2 | 2/2011 |
| WO | WO-2013027027 | A2 | 2/2013 |
| WO | WO-2014125250 | A1 | 8/2014 |
| WO | WO 2014131850 | A1 | 9/2014 |
| WO | WO 2014140994 | A1 | 9/2014 |
| WO | WO-2015049150 | A1 | 4/2015 |
| WO | WO-2015055709 | A1 | 4/2015 |
| WO | WO-2015/078735 | A1 | 6/2015 |
| WO | WO-2015/091582 | A1 | 6/2015 |
| WO | WO-2015172735 | A1 | 11/2015 |
| WO | WO-2016092290 | A1 | 6/2016 |
| WO | WO-2016094749 | A1 | 6/2016 |
| WO | WO-2016159151 | A1 | 10/2016 |
| WO | WO-2017125743 | A1 | 7/2017 |
| WO | WO-2017125744 | A1 | 7/2017 |
| WO | WO-2017125763 | A1 | 7/2017 |

OTHER PUBLICATIONS

Pisani-Real-time Automated Detection of Clonic Seizures in Newborns, Clinical Neurophysiology 125 (2014) 1533-1540.

Verkruysse-Remote Plethysmographic Imaging using Ambient Light, Optics Express (Dec. 22, 2008) vol. 16, No. 26.

International Search Report for PCT/GB2017/050126, ISA/EP, Rijswijk, NL, dated Apr. 20, 2017.

Written Opinion of the Isa for PCT/GB2017/050126, ISA/EP, Rijswijk, NL, dated Apr. 20. 2017.

UK IPO Search Report for GB priority application 1601217.1, Newport, South Wales, dated Jul. 25, 2016.

Nathalie M. El Nabbout et al, "Automatically Detecting and Tracking People Walking through a Transparent Door with Vision", Computer and Robot Vision, 2008. CRV '08. Canadian Conference on, IEEE, Piscataway, NJ, USA, May 28, 2008 (May 28, 2008), pp. 171-178.

Qiang Zhu et al, "Learning a Sparse, Corner-Based Representation for Corner-Based Representation for Time-varying Background Modeling" , Computer Vision, 2005. ICCV 2005. Tenth IEEE International Conference on Beijing, China Oct. 17-20, 2005, Piscataway, NJ, USA, IEEE, Los Alamitos, CA, USA, vol. 1, Oct. 17, 2005 (Oct. 17, 2005), pp. 678-685.

Konstantinos Avgerinakis et al, "Activity detection and recognition of daily living events", Proceedings of the 1st ACM International Workshop on Multimedia Indexing and Information Retrieval for Healthcare, MIIRH '13, Oct. 22, 2013 (Oct. 22, 2013), pp. 1-7.

Arindam Sikdar et al, "Computer-Vision-Guided Human Pulse Rate Estimation: A Review", IEEE Reviews in Biomedical Engineering, vol. 9, Sep. 16, 2016 (Sep. 16, 2016), pp. 91-105.

Yu Sun et al,"Photoplethysmography Revisited: From Contact to Noncontact, From Point to Imaging", IEEE Transactions on Biomedical Engineering, IEEE Service Center, Piscataway, NJ, USA, vol. 63, No. 3, Mar. 1, 2016 (Mar. 1, 2016), pp. 463-477.

Tongchi Zhou et al, "A study of relative motion point trajectories for action recognition", 2015 International Conference on Wireless Communications & Signal Processing (WCSP), IEEE, Oct. 15, 2015 (Oct. 15, 2015), pp. 1-5.

Hisato Aota et al, "Extracting objects by clustering of full pixel trajectories", Signal Processing and Multimedia Applications (SIGMAP), Proceedings of the 2010 International Conference on, IEEE, Jul. 26, 2010 (Jul. 26, 2010), pp. 65-72.

Shandong Wu et al, "A hierarchical motion trajectory signature descriptor", 2008 IEEE International Conference on Robotics and Automation. The Half-Day Workshop on: Towards Autonomous

(56) References Cited

OTHER PUBLICATIONS

Agriculture of Tomorrow, IEEE -Piscataway, NJ, USA, Piscataway, NJ, USA, May 19, 2008 (May 19, 2008), pp. 3070-3075.
Search Report for GB Application No. 1618828.6, dated Mar. 31, 2017.
International Search Report and Written Opinion for PCT/GB2017/053343, dated Jan. 4, 2018; ISA/EP.
International Search Report and Written Opinion for PCT/GB2017/052779, dated Nov. 10, 2017; ISA/EP.
Search Report for GB Application No. 1615899.0, dated Feb. 28, 2017.
International Preliminary Report on Patentability and Written Opinion regarding Applicaiton No. PCT/GB2017/052779 dated Mar. 19, 2019.
International Search Report for PCT/GB2017/050162, ISA/EP, Rijswijk, NL, dated Jul. 6, 2017.
Written Opinion of the ISA for PCT/GB2017/050162, ISA/EP, Rijswijk, NL, dated Jul. 6, 2017.
Search Report for Priority Application GB1601140.5, UK IPO, Newport, South Wales, dated Jul. 21, 2016.
International Search Report for PCT/GB2017/050127, ISA/EP, Rijswijk, NL, dated Mar. 28, 2017.
Written Opinion of the ISA for PCT/GB2017/050127, ISA/EP, Rijswijk, NL, dated Mar. 28, 2017.
UK IPO Search Report under Section 17(5) for priority application GB1061143.9, dated Mar. 30, 2016.
International Search Report for PCT/GB2017/050128, ISA/EP, Rijswijk, NL, dated Apr. 13, 2017.
Written Opinion of the ISA for PCT/GB2017/050128, ISA/EP, Rijswijk, NL, dated Apr. 13, 2017.
Search Report under Section 17(5) for priority application GB1601142.1, UKIPO, Newport, South Wales, dated Jun. 28, 2016.
Tarassenko et al, "Non-contact video-based vital sign monitoring using ambient light and auto-regressive models", 2014 Physiol. Meas. 35 807, pp. 807-831.
Wu et al, Eulerian Video Magnification for Revealing Subtle Changes in the World, 2012.
Search Report regarding United Kingdom Patent Application No. GB1706449.4, dated Oct. 25, 2017.
Amelard Robert et al. "Illumination-compensated non-contact imaging photoplethysmography via dual-mode temporally coded illumination". Progress in Biomedical Optics and Imaging, SPIE—International Society for Optical Engineering, Bellingham, WA, US., vol. 9316, Mar. 5, 2015.
Blocker Timon et al, "An online PPGI approach for camera based heart rate monitoring using beat-to-beat detection", 2017 IEEE Sensors Applications Symposium (SAS), IEEE, Mar. 13, 2017.
Extended European Search Report regarding applicaiton No. 18168310.3-1115 dated Oct. 1, 2018.
European Search Report regarding Application No. EP 19 15 8085 dated Jul. 10, 2019.
Nakajima, Kazuki, Yoshiaki Matsumoto, and Toshiyo Tamura. "Development of real-time image sequence analysis for evaluating posture change and respiratory rate of a subject in bed." Physiological Measurement 22.3 (2001).
Search Report of UKIPO regarding Application No. GB1900033.0 dated Jun. 13, 2019.
British Search Report regarding Appliction No. 1900034.8 dated Jun. 13, 2019.
Extended EP Search Report regarding Application No. 19220090.5 dated Feb. 24, 2020.

\* cited by examiner

SIGNAL PROCESSING METHOD AND APPARATUS

CROSS-REFERENCE TO RELATED APPLICATIONS

This application is a 371 U.S. National Stage of International Application No. PCT/GB2017/050126, filed Jan. 19, 2017, which claims priority to British Patent Application No. 1601217.1, filed Jan. 22, 2016. The entire disclosures of the above applications are incorporated herein by reference.

The present invention relates to a method and apparatus for processing digital signals, more particularly for combining time segments of processed signals together to provide a continuous output signal.

In the field of digital signal processing it is common to divide an input signal consisting of a stream of sample values into successive batches, corresponding to time windows, with each batch overlapping the preceding one. Effectively this corresponds to taking a time window of the signal, processing that time window, then moving the time window on by some increment and processing the signal from that new time window. It is desirable, however, to provide, in some applications, a continuous output signal. This may be achieved by taking the processed results from each time window and combining them together in a corresponding temporal sequence. For example, U.S. Pat. Nos. 8,855,384 and 9,036,877 disclose methods of "stitching together" signal segments to provide a continuous output signal.

A problem arises though in that the methods used to stitch signal segments together can result in the introduction of signal artefacts, particularly around the end of time windows, or that the output does not faithfully follow the input where there are significant and fast changes in the input signal. Also many existing methods cannot be employed to produce such a continuous output in real time because of the amount of processing required.

A first aspect of the present invention provides a method and corresponding apparatus for combining together the processed signals from several successive time windows in real time in a way which avoids introducing artefacts and which more faithfully reflects the input signal. This is achieved by forming as each successive output signal value a weighted sum of the preceding output signal value and the differential of the signal.

Another aspect of the invention provides a method and apparatus which combines multiple simultaneous signals thought to contain a common periodic component by finding the strength of a periodic component in each of the signals, and then adding the multiple signals together in a weighted sum according to the strength of the periodic component in each signal. Thus the sum favours those signals with a strong periodic component. Preferably the strength of the periodic component is measured after filtering each of the signals with a filter passing the frequencies of interest. The sum, however, is preferably of the weighted unfiltered signals.

In more detail the first aspect of the invention provides a method of combining together successive temporal signal segments of a physiological signal, each segment comprising a plurality of successive signal sample values, to provide a continuous output stream of signal values, the method comprising the steps of: acquiring a plurality of successive signal segments; differentiating the signal in each successive signal segment; forming said continuous output stream of signal values by outputting as the current signal value a weighted sum of the previous output sample signal value and the differential of the signal. By weighted sum is meant that at least one of the previous output sample signal value and the differential of the signal contribute to the sum in a weight which is not unity.

The weights associated with one or both of the components of the weighted sum may in one embodiment be calculated according to the variability and/or average value that the signal has recently taken.

Preferably the weight of the differential in the weighted sum is based on at least one of: the variability in the signal, the average value, e.g. mean or median, of a predetermined number of previous output sample signals, a maximum (largest) value of a predetermined number of previous output sample signals, a minimum (smallest) value of a predetermined number of previous output sample signals.

Preferably the variability in the signal is measured over a predetermined number of preceding values of the differential signal, e.g. 10 to 50 sample values, more preferably 15 to 30, for example 20 sample values. This corresponds in a signal with 20 samples per second to a time period of about 0.5 to 2.5 seconds. The predetermined number of values is chosen according to the nature of the signal, e.g. its periodicity and/or temporal variability Preferably the weight of the previous output sample signal in the weighted sum is based on the variability in the signal, which again may be measured over a few, e.g. 10 to 50 sample values.

Preferably an initial segment of an acquired signal is output as an initial sequence of output signal values, subsequent values of the output signal being formed by differentiating subsequent segments of the acquired signal and performing said summing and inversely weighting steps.

Preferably said successive temporal signal segments are time windows, each time window partly overlapping the preceding time window, and said steps of summing and inversely weighting are performed on those signal values in the time window which are not overlapping with the preceding time window The signal segments may each be formed from a combination of contemporaneous source signals The combination of source signals is a weighted combination of the source signals, with a the weight of each source signal being in accordance with the strength of a periodic physiological component in the source signal just as in the second aspect of the invention.

In the second aspect of the invention the weight of each source signal in the combination may be obtained in a method comprising the steps of performing principal component analysis on the source signals and calculating the contribution of each of said signals to the first principal component. Preferably the weight of the periodic component is the weight of the periodic component in filtered versions of the source signals.

The filtered versions of the source signals may be obtained by bandpass filtering them. The passband of the bandpass filter is preferably the expected frequency range of the physiological signal.

The step of forming the weighted combination of source signals may comprise combining the unfiltered source signals in accordance with the strength of the periodic physiological signal in the filtered signals. An advantage of combining unfiltered signals is that it can avoid artefacts created by the filtering process when there is a significant change in the source signals.

In any aspect of the invention the signals may be measurements acquired from a human or animal subject and contain the physiological signal. The measurements may be measurements of movement of the body of the human or animal subject. The measurements may be obtained by analysis of a video image sequence of the subject, for example by feature tracking through the video image sequence, or by measuring changes in image intensity in regions of interest in frames of the video mage sequence, which may comprise a photoplethysmographic signal.

The invention may provide apparatus adapted to execute the method the invention and comprising: a signal input for receiving the signals, a data processor for processing the signals and a signal output for outputting the signals. The invention may be embodied in a computer program comprising program code means for executing the steps of the method. The invention will be further described by way of example with reference to the accompanying drawings in which:—

An embodiment of the invention will now be described in the field of physiological monitoring. An enormous number of techniques are available for physiological monitoring of a human or animal. There are many techniques for obtaining signals which contain some periodic physiological signal of interest, such as a signal representative of a vital sign such as breathing or cardiac activity and these may be based on the use of sensors which contact the subject, such as a classic photoplethysmographic (PPG) sensor which can be attached to the finger or earlobe and provides a signal representing the variations in blood volume in the tissue adjacent the sensor, this signal containing components of the heart rate and breathing rate, or more recently various camera-based non-contact methodologies for obtaining signals including components corresponding to the heart beat or to breathing. Typically, however, the signals are noisy and it is difficult to separate out the physiological signal of interest to produce an accurate estimate of the corresponding physiological parameter, such as the heart rate or breathing rate.

Figure 9:
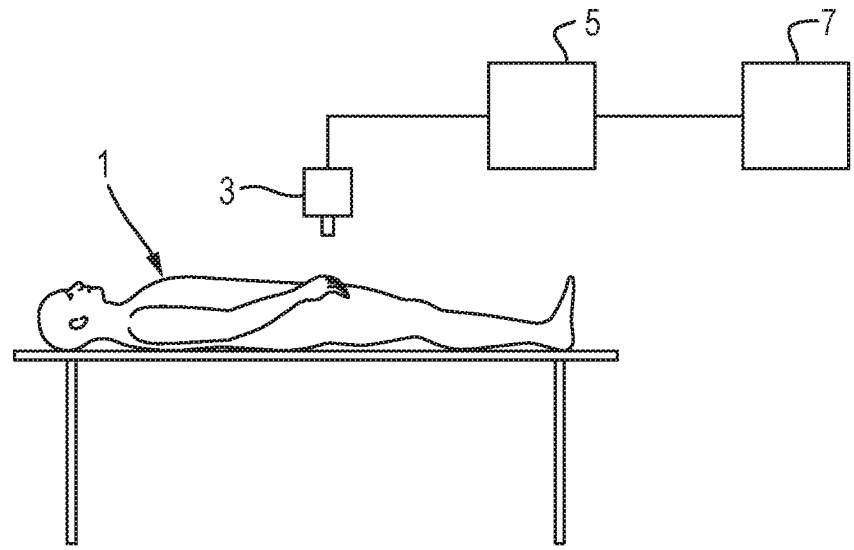
FIG. 9 illustrates the apparatus of one embodiment of the invention.
Figure 10:
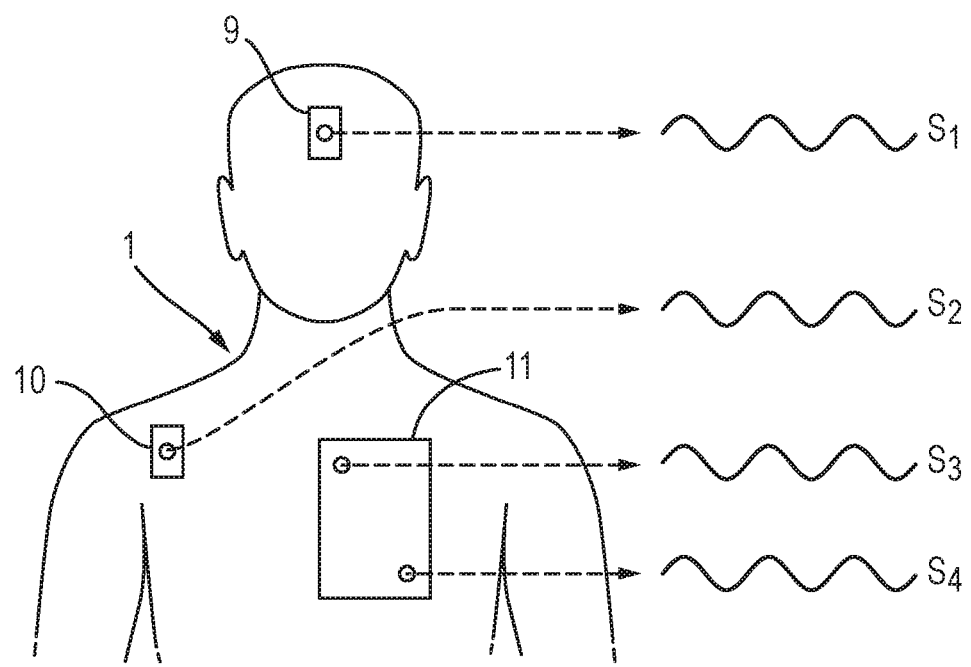
FIG. 10 illustrates a subject with regions of interest defined thereon in accordance with an embodiment of the invention.

In various methodologies several signals may be obtained from the same subject at the same time, each of them containing a component corresponding to the physiological signal of interest. For example, as illustrated in FIG. 9 a subject 1 may be monitored by a video camera 3 whose output is passed to a data processor 5 adapted to extract from the video signals estimates of certain physiological parameters of the subject such as the heart rate or breathing rate which can be displayed on the display 7. As illustrated in FIG. 10 this may be achieved by defining several regions of interest 9, 10 and 11 on the subject, which may be on the skin or on clothing or other articles in contact with the subject and processing the video signals from these regions of interest to find the periodic physical signals of interest. Each region of interest might provide one signal, such as $S_1$ and $S_2$ in FIG. 10, or a single region of interest may provide several signals, such as $S_3$ and $S_4$. The signals may, for example, be image intensity signals in one or more colour channels which may contain a PPG component, or may be movement signals, i.e. the spatial coordinates of some feature which is tracked through the sequence of video images.

The present invention allows such plural signals, each of which are typically divided into plural overlapping time windows for processing, to be recombined in real time to provide a continuous, real time output estimate of the physiological parameter of interest.

Figure 1:
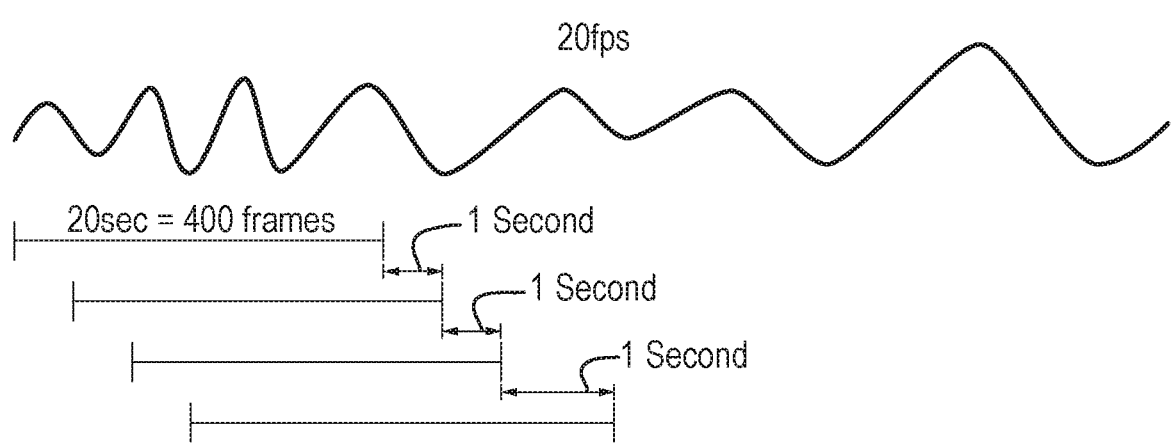
FIG. 1 illustrates an example input signal and the arrangement of a series of overlapping time windows.

As illustrated in FIG. 1, and as typical in digital signal processing, it is conventional to divide the stream of values forming each signal into batches, each corresponding to a time window of a certain length. FIG. 1 illustrates that a signal $S_1$, for example which corresponds to the spatial coordinates of a feature tracked through the video sequence, is divided into a succession of forty second time windows, each window being moved along by one second, and thus overlapping by thirty-nine seconds. For a typical video frame rate of forty frames per second, each time window would thus contain four hundred frames of data. In this example this would correspond to four hundred successive spatial positions of the tracked feature, but in a PPG signal it could be approximately 180 successive intensity values.

Figure 2:
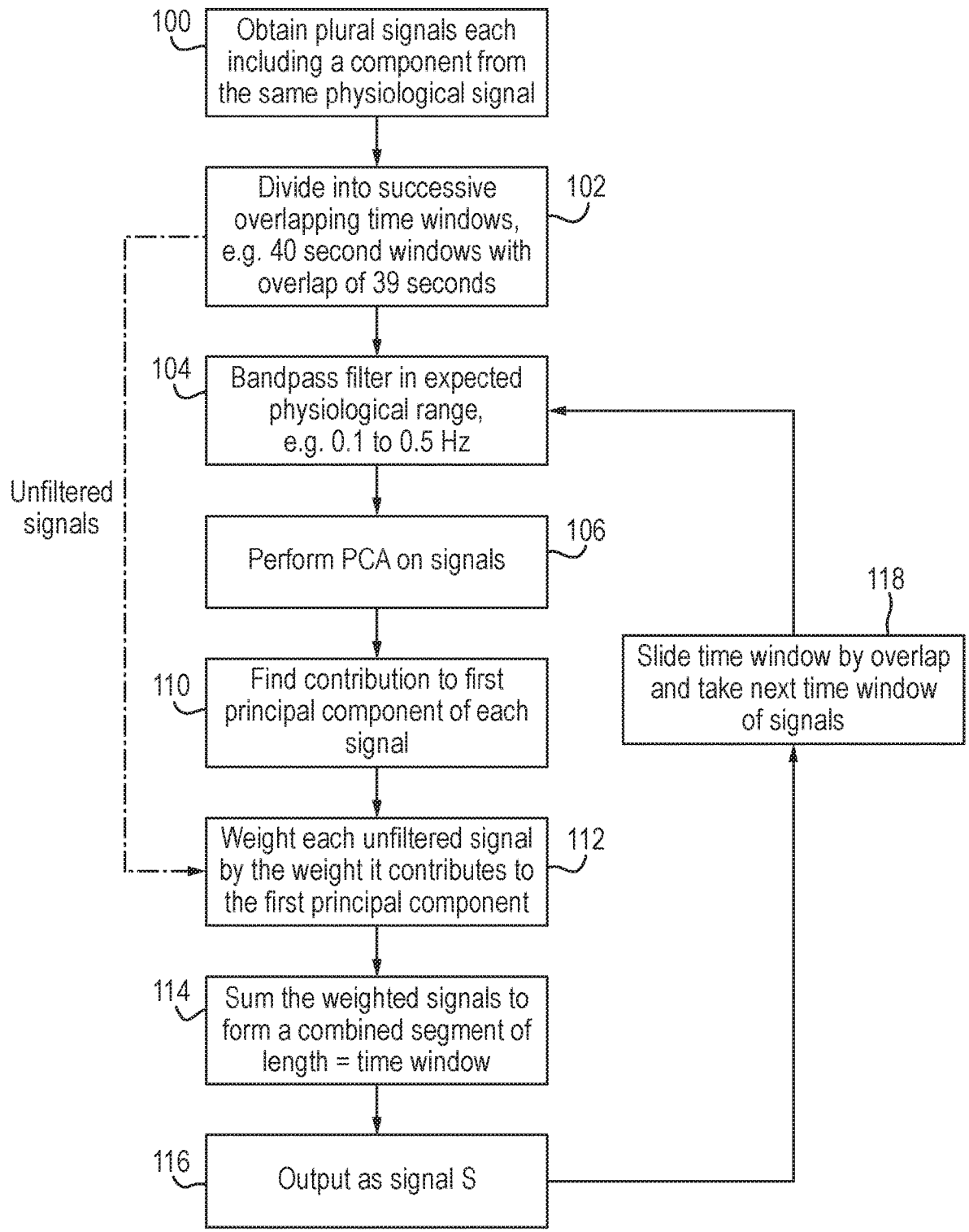
FIG. 2 is a flow diagram illustrating one embodiment of signal processing applied to a physiological signal.

In this embodiment of the invention, each of the plural signals obtained by the monitoring system (such as signals $S_1$ to $S_4$ in FIG. 10) is divided into time windows, and the temporally corresponding time windows from each of the plural signals are then combined together to form a single combined signal time window as illustrated in FIG. 2.

As illustrated in FIG. 2 in step 100 the plural signals are acquired, each thought to include a contribution from the physiological signal of interest and in step 102 each signal is divided into successive overlapping time windows.

Figure 4:
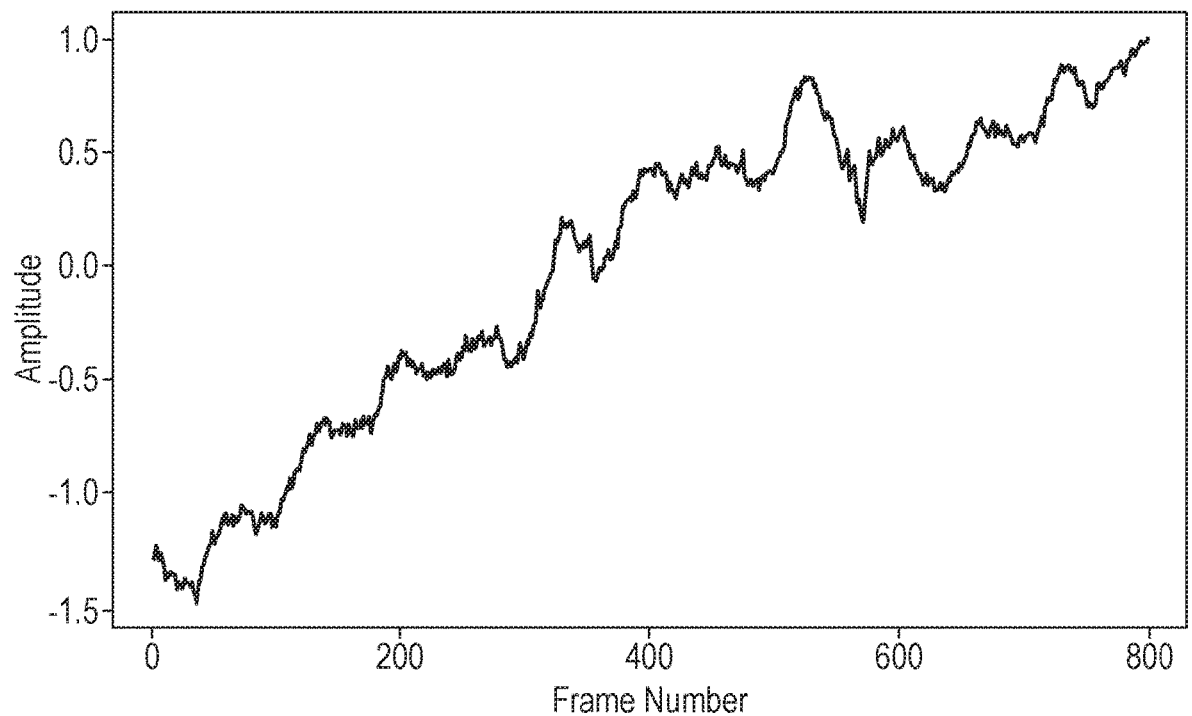
FIG. 4 illustrates the first principal component of an unfiltered signal on which an embodiment of the present invention was applied.
Figure 6:
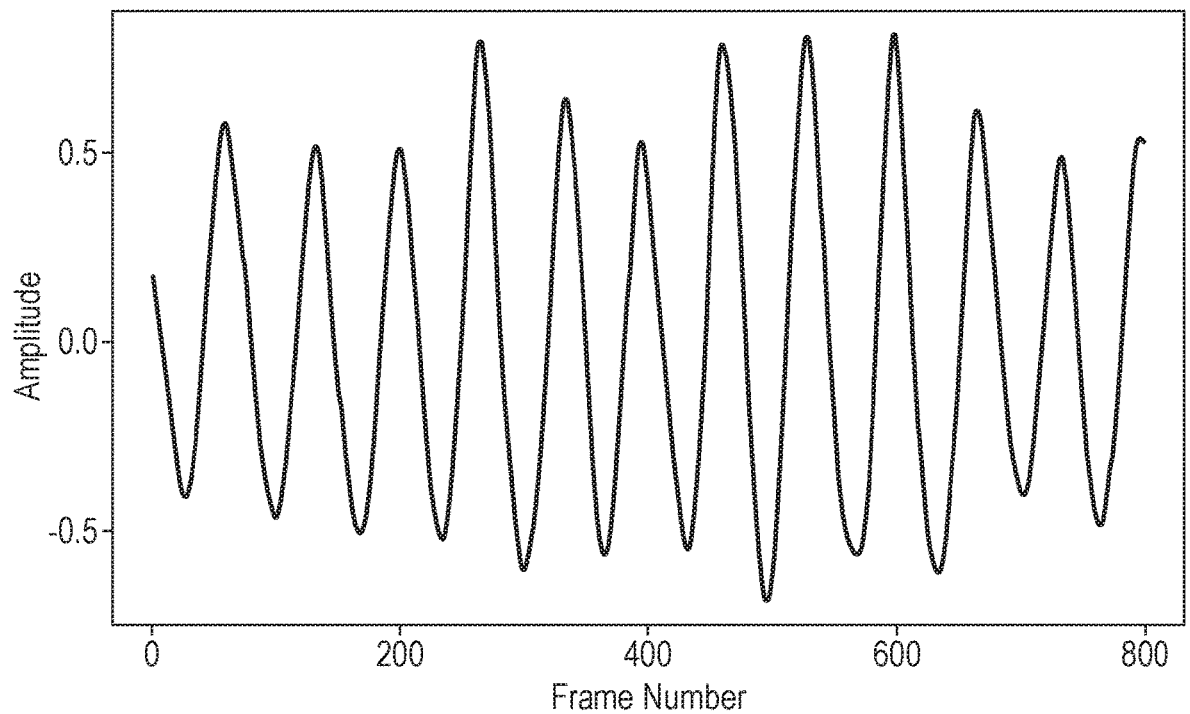
FIG. 6 illustrates the first principal component of the filtered signal.

In step 104 within each time window, each signal is then band-pass filtered, e.g. using a standard Butterworth filter, using the expected physiological range of the physiological parameter of interest. For detecting breathing, for example, the physiologically expected range is 0.1 Hz to 0.5 Hz. In step 106 principal component analysis (PCA) is performed on the signals and the weights associated with the first principal component are found. FIG. 6 of the accompanying drawings illustrates an example first principal component of an input signal thought to contain a human breathing rate component. For comparison, FIG. 4 illustrates the first principal component of an unfiltered signal and it can be seen that it contains a very low frequency component—appearing in the figure as an increasing trend across the trace—which is unlikely to be associated with breathing and undesirably masks the breathing component more clearly visible in the first principal component of the filtered signal shown in FIG. 6.

Figure 5:
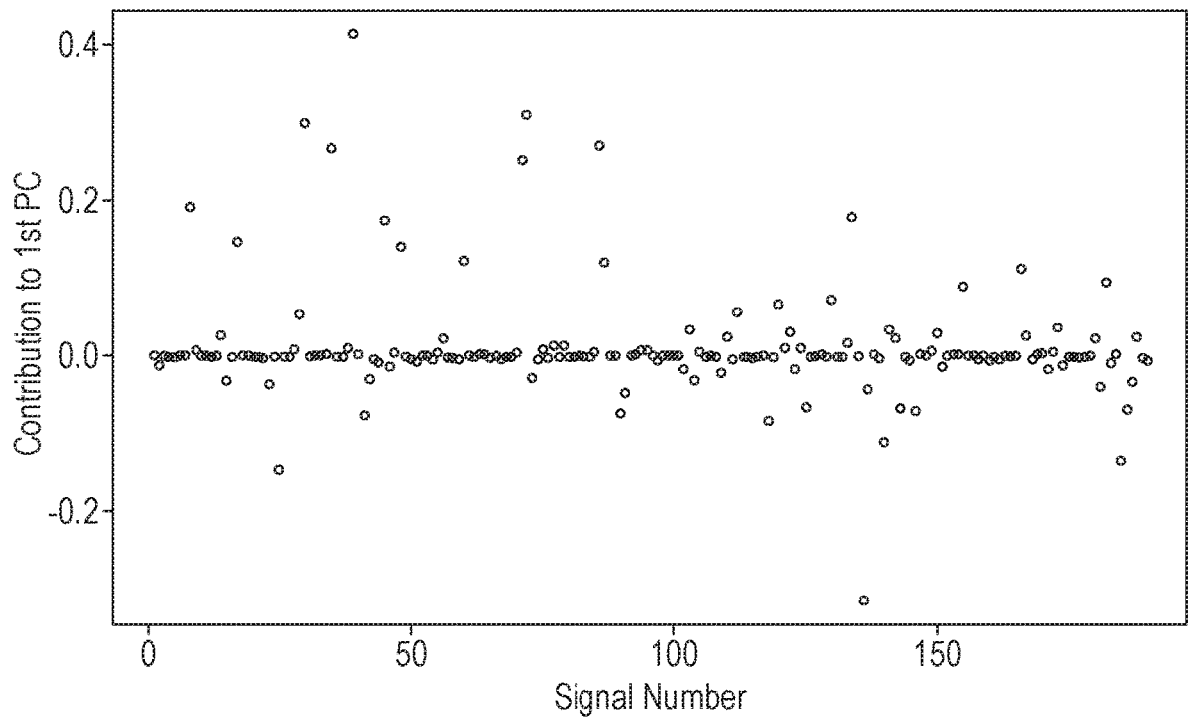
FIG. 5 illustrates the extent to which each of a plurality of signals contribute to the first principal component of the filtered signal shown in FIG. 6.

In step 110, the contribution to the first principal component from each of the signals is found. FIG. 5 illustrates the weights of the first principal component of FIG. 6 found in an example set of nearly two hundred signals from a forty second long (800 frames) video sequence of a human subject breathing. This video sequence is from a video monitor of a mocked-up secure room. A single subject was lying on a bed in the dark under IR illumination. Initially the subject was breathing normally, as one might expect to observe during undisturbed sleep. After some time (20 seconds into FIG. 8) the subject began holding their breath, so as to simulate abnormal breathing, similar to that which might occur in, say, sleep apnoea. Each of the nearly two hundred signals correspond to the movement of a feature point within the video, with some of these feature points located chest of the subject.

In step 112 the original unfiltered signals are each multiplied by their weight according to the first principal component and then linearly summed together. This means that in the resultant combined signal, those input signals which had a strong periodic component in the expected physiological range are favoured over those which do not have a strong periodic component in the expected physiological range.

This creates in step 114 a forty second signal segment resulting from the weighted combination of all the original (unfiltered) input signals. This forty second combined signal is output in step 116 and in step 118 the time window is moved by the required time increment, for example one second, and the process repeated to produce the next combined signal time window.

The output of the process of FIG. 2 will therefore be a succession of forty second signal segments (each produced by combining several individual signal's time windows together) overlapping by, in this case, thirty-nine seconds. From these it is desirable to output a continuous signal. Various proposals have been made in the prior art for combining the signals in such overlapping time windows, but it is difficult, as mentioned above, to avoid creating artefacts in the combining process.

Figure 3:
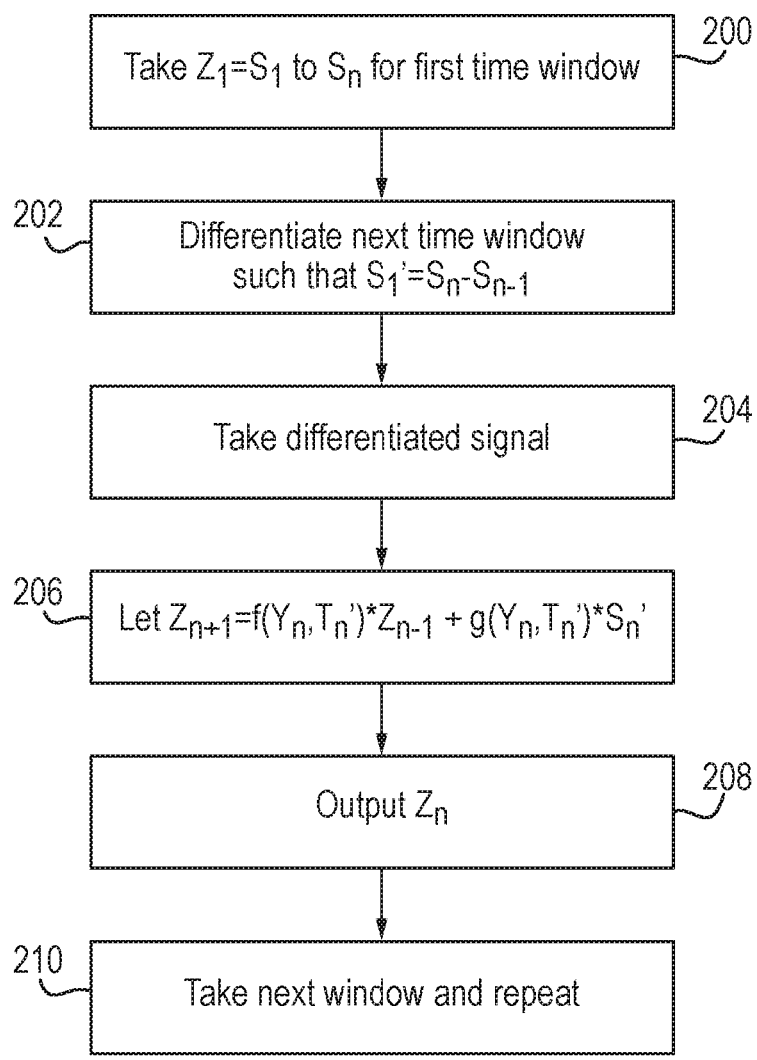
FIG. 3 is a flow diagram illustrating one embodiment of forming an output signal from the signals from plural overlapping time windows.

FIG. 3 illustrates how the successive segments are combined in accordance with one embodiment of the invention. In step 200, the first time window signal is taken in its entirety. In this example, this corresponds to forty seconds worth of signal, or the first eight hundred frames. This will form the first section $Z_1$ (40 seconds) of the output signal Z. In step 202, the signal in the next time window is differentiated by finding the differences between each successive pair of signal values, i.e. $S'_n = S_n - S_{n-1}$. Then in step 204, the values of the differentiated signal for the portion of the time window which is non-overlapping with the previous window (i.e. the last second, corresponding to the last twenty frames, in this case) are taken (i.e. $S'_{801}$ to $S'_{820}$). Then a new output signal value is calculated for each time point, as a function of Z and S', as explained below, and for which in at least some cases $Z_n \neq Z_{n-1} + S'n$.

The function used to derive $Z_n$ can take as inputs only $Z_{n-1}$, $S'_n$ and $T'_n$ where $T'_n$ is a measure of the variability in the signal S. One example of $T'_n$ is the mean of the magnitude of the derivative, i.e. mean of $|S'|$, over a number of preceding values, say, indices n to n−19. A second example of $T'_n$ can be evaluated as follows: Let M be a function, such as a Gaussian smoother, which takes as input a vector and outputs a smoothed version of the input vector. Let U be a smoothed version of the absolute value of the differences in the smoothed values of S; $U=M(|M(S)'|)$. Then if $U_n > c$, for some chosen constant c, the value of $T'_n$ is set to be equal to $U_n$, or 0 otherwise.

The function used to derive $Z_n$ can take as inputs only $Z_{n-1}$, $Y_n$, $S'_n$ and $T'_n$ where $Y_n$ is a measure of the mean value that Z has recently taken. One example of $Y_n$ is the mean or median of Z evaluated over a number of preceding values, say, indices n to n−19. A second example sets $Y_n = \min(Z)$ if $\min(Z) > 0$, $Y_n = \max(Z)$ if $\max(Z) < 0$, or $Y_n = 0$ otherwise, where in all cases the min and max values are assessed over a number of preceding values, say, indices n to n−19.

To calculate $Z_n$, given $Z_{n-1}$, $S'_n$ and $T'_n$, and optionally also $Y_n$, let f and g be generic functions of $Y_n$, $T'_n$ and $S'_n$, for which $g(Y_n, T'_n, S'_n) > 0$ and $0 < f(Y_n, T'_n, S'_n) \leq 1$. Then the function used to calculate $Z_n$ may be further constrained to be of the form:

$$Z_n = f(Y_n, T'_n) * Z_{n-1} + g(Y_n, T'_n) * S'_n, \qquad \text{Equation 1}$$

for which in at least some cases at least one of $f(Y_n, T'_n)) \neq 1$ or $g(Y_n, T'_n) \neq 1$.

The functions $f(Y_n, T'_n, S'_n)$ and $g(Y_n, T'_n, S'_n)$ can be monotonically decreasing functions of $Y_n$, $|T'_n|$ and S'n. Examples of f and g include, but are not limited to:

$f = 1/(1+|S'_n|)$, $g = 1/(1+|S'_n|)$, $f = 1$ and $g = 1/(1+\min(c*|Y_n*T'_n|,1))$ if $Y_n*S'_n > 0$, or $g = (1+\min(c*|Y_n*T'_n|,1))$, otherwise, for some constant c>0.

The resulting values from using Equation 1, e.g. $f = 1/(1+|S'_n|)$ and $g = 1/(1+|S'_n|)$ are output as the output signal Z for frame numbers 401 to 420 as illustrated in step 208. As indicated in step 210 the process is then repeated for the last, non-overlapping part of the next time window.

Thus, for the start of an acquired signal, the first part of the output signal Z corresponds to the initial time window. For each time window increment or step thereafter, the output at each time point (corresponding to each frame in this embodiment) corresponds to a sum of the preceding output signal value Z with the value of the differential of the signal S' at that point, downweighted by a value based on the amplitude of the differential. Each successive time window contributes a successive time period of output signal Z which is contiguous with the preceding signal and so a continuous output is obtained. Furthermore, the processing is simple and only relies on the signal values within each time window, and thus can be done in real time.

Depending on the form of the output signal, the physiological parameter of interest can be derived from it. For example, if the signal is representative of breathing movement, the frequency of the signal can be measured (by measuring peak to peak times, or by finding the strongest peak in a Fourier Transform of the signal for example) and the breathing rate in breaths per minute calculated by multiplying the frequency by frequency in Hertz by sixty.

Figure 7:
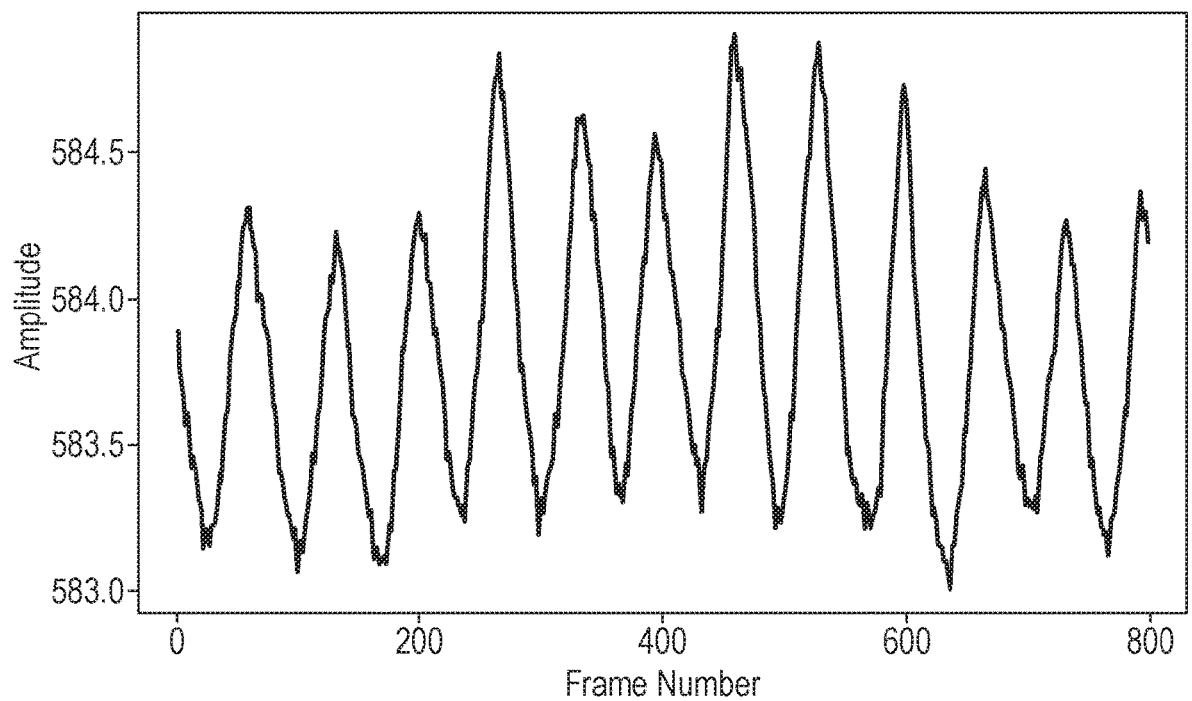
FIG. 7 illustrates the results of combining the unfiltered signals using weights according to the first principal component from the filtered signal.

FIG. 7 illustrates the results of adding two hundred signals from a video image sequence in an example of the invention together weighted by the first principal component weights as illustrated in FIG. 5. Thus FIG. 7 is the result of applying the process of FIG. 2 to example breathing movement signals.

Figure 8:
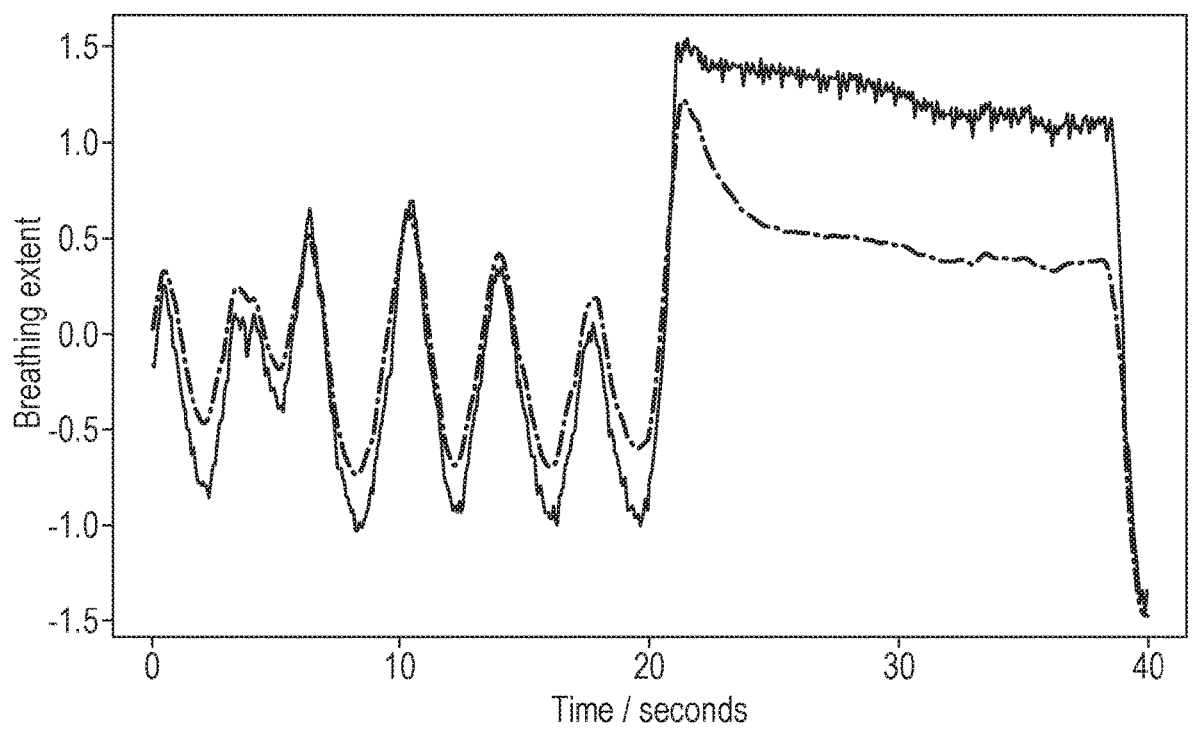
FIG. 8 illustrates an output signal formed by combining plural input signals in accordance with an embodiment of the invention.

FIG. 8 illustrates the results of applying the processing of FIG. 3 to such a breathing movement signal for a period of forty seconds in which the last twenty seconds correspond to the subject holding their breath. The red trace corresponds to combining unfiltered signals according to the weights they contribute to the first principal component of the filtered signals, in accordance with the method above. As can be seen, the signal clearly shows the periodic breathing movement for the first twenty seconds and faithfully shows the lack of periodic breathing movement for the breath hold from twenty to forty seconds.

The black trace shows, for comparison, the effect of combining filtered signals (again according to the weights they contribute to the first principal component of the filtered signals). In this case the combined filtered signals undershoot the correct values, this being an artefact of the filtering process when there is a change in the breathing pattern, as filtering tends to attenuate the ends of the time windows.

Although the invention has been described with reference to the combining of physiological signals thought to contain a breathing movement component, it is applicable to signals which contain components corresponding to other physiological signals, such as the cardiac cycle.

The invention may be embodied in a signal processing method, or in a signal processing apparatus which may be constructed as dedicated hardware or by means of a programmed general purpose computer or programmable digital signal processor. The invention also extends to a computer program for executing the method.

The invention claimed is:

1. A method of combining together multiple simultaneous source signals thought to contain a common physiological signal, the method comprising the steps of:
    acquiring a plurality of successive signal segments of each of the multiple simultaneous source signals, each segment comprising a plurality of successive signal sample values;
    bandpass filtering the multiple simultaneous source signals;
    determining a strength of a periodic physiological component in contemporaneous segments of the bandpass filtered signals; and
    forming as an output signal segment a weighted combination of an unfiltered contemporaneous signal segments of the multiple simultaneous source signals with a weight of each segment being in accordance with the strength of the periodic physiological component in a bandpass filtered version of the segment.

2. The method according to claim 1 wherein the weight of the differential in the weighted sum is based on at least one of: the variability in the signal, the average value of a predetermined number of previous output sample signals, a maximum value of a predetermined number of previous output sample signals, a minimum value of a predetermined number of previous output sample signals.

3. The method according to claim 2 wherein the variability in the signal is measured over a predetermined number of preceding values of the signal.

4. The method according to claim 1, wherein the weight of the previous output sample signal in the weighted sum is based on the signal variability.

5. The method according to claim 1, wherein an initial segment of an acquired signal is output as an initial sequence of output signal values, subsequent values of the output signal being formed by differentiating subsequent segments of the acquired signal and performing said summing and inversely weighting steps.

6. The method according to claim 1, wherein said successive temporal signal segments are time windows, each time window partly overlapping the preceding time window, and said steps of summing and inversely weighting are performed on those signal values in the time window which are not overlapping with the preceding time window.

7. The method according to claim 1, wherein the weight of each source signal in the combination is obtained in a method comprising the steps of performing principal component analysis on the source signals and calculating a contribution of each of said signals to a first principal component.

8. The method according to claim 1, wherein a passband of the bandpass filter is an expected frequency range of the physiological signal.

9. The method according to claim 1, wherein the signals are measurements acquired from a human or animal subject and contain the physiological signal.

10. The method according to claim 9, wherein the measurements are measurements of movement of the body of the human or animal subject.

11. The method according to claim 9, wherein the measurements are obtained by analysis of a video image sequence of the subject.

12. The method according to claim 11, wherein the analysis comprises feature tracking through the video image sequence.

13. The method according to claim 11, wherein the analysis comprises measuring changes in image intensity in regions of interest in frames of the video image sequence.

14. The method according to claim 13, wherein the changes in image intensity comprise a photoplethysmographic signal.

15. The method according to claim 1, further comprising the step of forming a continuous output stream of signal values by outputting as a current signal value a weighted sum of a previous output sample signal value and the differential of the output signal segment.

16. An apparatus comprising:
    a signal input for receiving a physiological signal,
    a data processor for processing the signal and adapted to combine together multiple simultaneous source signals thought to contain a common physiological signal, by;
        acquiring a plurality of successive signal segments of each of the multiple simultaneous source signals, each segment comprising a plurality of successive signal sample values,
        bandpass filtering the multiple simultaneous source signals, determining a strength of a periodic physiological component in contemporaneous segments of the bandpass filtered signals, and
        forming as an output signal segment a weighted combination of an unfiltered contemporaneous signal segments of the multiple simultaneous source signals with a weight of each segment being in accordance with the strength of the periodic physiological component in a bandpass filtered version of the segment, and
    a signal output for outputting the signals.

17. A computer program comprising program code means for executing the steps of combining together multiple simultaneous source signals thought to contain a common physiological signal, by:
    acquiring a plurality of successive signal segments of each of the multiple simultaneous source signals, each segment comprising a plurality of successive signal sample values,
    bandpass filtering the multiple simultaneous source signals, determining a strength of a periodic physiological component in contemporaneous segment of the bandpass filtered signals, and
    forming as an output signal segment a weighted combination of an unfiltered contemporaneous signal segments of the multiple simultaneous source signals with a weight of each segment being in accordance with the strength of the periodic physiological component in a bandpass filtered version of the segment.

* * * * *